United States Patent
Heinz et al.

(10) Patent No.: US 6,602,214 B2
(45) Date of Patent: *Aug. 5, 2003

(54) ORTHOTIC TRAUMA DEVICE

(75) Inventors: Thomas J. Heinz, Flintridge, CA (US);
Dae Shik Park, Fullerton, CA (US);
Rafn Stefansson, San Marino, CA (US)

(73) Assignee: Bio Cybernetics International, Pasadena, CA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/420,408

(22) Filed: Oct. 19, 1999

(65) Prior Publication Data

US 2002/0148461 A1 Oct. 17, 2002

(51) Int. Cl.[7] .................. A61F 5/00; A61F 5/28
(52) U.S. Cl. ......................... 602/19; 128/99.1
(58) Field of Search ................ 602/5, 19, 20, 602/23, 60–65; 128/845–846, 869–870, 874–875, 878, 881–882; 606/201, 203; 2/311–312, 44; 178/99.1, 100.1, 101.1, 102.1

(56) References Cited

U.S. PATENT DOCUMENTS

| | | | |
|---|---|---|---|
| 232,420 A | 9/1880 | Smith | |
| 321,146 A | 6/1885 | Spencer | |
| 571,749 A | 11/1896 | Colton | |
| 715,935 A | * 12/1902 | Alvord | |
| 746,563 A | 12/1903 | McMahon | |
| 787,894 A | 4/1905 | Colton | |
| 894,066 A | 7/1908 | Scarpa | |
| 1,469,661 A | 10/1923 | Migita | |
| 1,530,713 A | 3/1925 | Clark | |
| 2,036,484 A | 4/1936 | Le May | |
| 2,100,964 A | 11/1937 | Kendrick | |
| 2,219,475 A | 10/1940 | Flaherty | |
| 2,554,337 A | * 5/1951 | Lampert | 128/96 |
| 4,459,979 A | * 7/1984 | Lewis, Jr. | 128/78 |
| 4,508,110 A | * 4/1985 | Modglin | 128/78 |
| 5,036,864 A | * 8/1991 | Yewer, Jr. | 128/876 |
| 5,399,151 A | 3/1995 | Smith | |
| 5,469,640 A | * 11/1995 | Nichols | 36/50.1 |
| 5,499,965 A | 3/1996 | Sanchez | |
| 5,599,287 A | 2/1997 | Beczak, Sr. et al. | |
| 5,814,002 A | * 9/1998 | Nelson | 602/27 |

(List continued on next page.)

FOREIGN PATENT DOCUMENTS

KR   20-0146563   2/1999

Primary Examiner—Denise M. Pothier
(74) Attorney, Agent, or Firm—Arent Fox Kintner Plotkin & Kahn

(57) ABSTRACT

An orthotic trauma device is provided including an elongated orthosis body adapted to be wrapped around a portion of a body, the orthosis body being formed of a pliant material be easily cut with cloth-cutting scissors; a detachable fastening device provided at distal ends of the elongated orthosis body to releasably secure the distal ends to one another; and means for adjusting the tightness of the orthosis body operatively associated with the detachable fastening device. A pulley system for use in an orthotic device includes a pair of pulley banks arranged in a first and second of the pair of pulley banks detachably connected to a first distal end and a second distal end of the orthosis body respectively, a first bank of which is adapted to be detachably disposed on a first distal end of an elongated orthosis body and a second bank of pulleys adapted to be detachably disposed on a second distal end of the elongated orthosis body; and a cable interconnecting the two pulley banks and running through a pulley on each of the pulley banks in alteration, such that shortening of the cable pulls the pulley banks together and tightens the orthotic device with the aid of a mechanical advantage.

18 Claims, 3 Drawing Sheets

U.S. PATENT DOCUMENTS 5,843,008 A * 12/1998 Gerhard .......................... 602/5
5,853,378 A * 12/1998 Modglin ....................... 602/19
5,970,526 A * 10/1999 Weathers ....................... 2/321
6,024,712 A *  2/2000 Iglesias et al. ................. 602/6
6,190,343 B1 *  2/2001 Heinz et al. ................... 602/19
6,213,968 B1 *  4/2001 Heinz et al. ................... 602/19
6,517,502 B2 *  2/2003 Heyman et al. ............... 602/5

* cited by examiner

ORTHOTIC TRAUMA DEVICE

TECHNICAL FIELD

The invention relates to orthotic devices which may be used in the emergency treatment of bone fractures. More particularly, the invention relates to orthotic devices for partial or substantial immobilization of bone fractures, and particularly pelvic fractures, in emergency rooms of hospitals, at an accident site or in transit from an accident site, where quick and effective stabilization of a fracture is essential and where such a device must be adapted both to the dimensions of the individual and the body part being treated.

BACKGROUND ART

A common method of treating fractures in the field or at an accident scene is to determine the nature and general extent of the injury and thereafter attempt to immobilize the fractured body part to avoid further injury to the patient, should the body part be moved. Although it may be appropriate to immobilize bone fractures of a limb with a cast arrangement at an accident scene, because of the nature of the type of materials used to form such casts and the time required to apply and subsequently remove the cast when the patient reaches the hospital or other treatment facility, it is generally not feasible to attempt to immobilize pelvic fractures by such means. In addition, without the benefit of x-ray pictures of the injured area, the fracture could be improperly immobilized, causing additional harm. Little more can be done in the field since the means to produce x-ray pictures of the fracture at the accident scene are currently unavailable. Should the patient be bleeding, additional steps may be taken to arrest bleeding.

Although exceptions exist, the time elapsed between the occurrence of the fracture of a limb and the subsequent treatment of the limb in a modern medical facility does not result in a life threatening situation as long as the treatment in such a facility is not unduly delayed, the patient has not lost a large volume of blood, and initial emergency treatment has been administered in the interim. However this is not true of bone fractures in other parts of the body, particularly in the pelvic region.

Tens of thousands of pelvic fractures occur each year. Most of these injuries result from motor vehicle collisions, falls from height, or other industrial accidents. Many of these injuries are life threatening with serve blood loss from torn blood vessels or bleeding from fractured pelvic bones. Even with hairline pelvic fractures, blood loss may be significant since the pelvis bones are very porous.

Heretofore, emergency treatment for these injuries has required the application of a pelvic external fixator. To properly apply the device, pins must be drilled into the pelvic bones and connected to a frame by clamps. Accordingly, successful application of a pelvic external fixator requires experienced personnel and frequently X-ray fluoroscopic control. Usually these devices are applied in the operating room of a hospital. Presently, there is no means of stabilization of pelvic fractures by emergency medical service technicians for transport of the patients from the accident scene.

Thus, a need exists for a device and a method of rapidly immobilizing a fractured bone and particularly a fractured pelvic bone. A need also exists for a method and device which can be used to supply sufficient pressure at the site of the fracture to arrest any bleeding that accompanies the fracture, particularly a fractured pelvic bone. Any device and method used for such purposes should, preferably, also be easily and quickly administered to the patient with little regard to the dimensions of the patient or the strength of the medical treatment personnel. In addition, a significantly higher skill level should not be required of the emergency personnel applying such a device to a patient suffering from a bone fracture than is generally required from such personnel at the present time in treating the same type of fracture. Preferably, the device should be capable of being left in place both during the early stages of emergency treatment and through initial assessment of the degree of injury and proposed treatment. This would include conducting an x-ray examination and, accordingly, preferably, the device should not include any radio-opaque materials. In addition, the device should be preferably so constructed and formed from such materials as to permit the device to conform to the profile and the dimensions of the part of the body to which it is applied. Accordingly, except where a stay or splint type of article is to be operatively associated with the device, no rigid parts should be incorporated into the device. Preferably, the device should also apply pressure substantially equally to all surfaces of the portion of the body which it contacts.

It is an object of the invention to provide orthoses and a method of using such orthoses to rapidly immobilize a fractured bone, particularly a fractured pelvic bone. It is a further object of the present invention to employ a single orthotic device to permit custom fitting of the device to patients and body parts of different sizes. It is an additional object to provide an orthotic trauma device and a method of using the same which can provide sufficient pressure at the site of the injury to arrest bleeding accompanying a bone fracture. It is an object of this invention to provide an orthotic device which can be easily and quickly administered to a patient with little regard to the dimensions of the patient or the strength of the medical treatment personnel treating the patient. More specifically, it is a primary object of this invention to provide orthoses which may be tightened around the fractured bone of a patient to provide the necessary support with minimal physical effort required on the part of the emergency medical treatment personnel. It is yet another object of the present invention to provide apparatus having a significant mechanical advantage that may be individually adjusted to a desired tension and conformity to an individual patient's dimensions. In addition, it is an object of the invention to require a skill level of the emergency personnel applying such a device to a patient suffering from a bone fracture which is not significantly higher than is generally required from such personnel at the present time in treating the same type of fracture using currently available means for such treatment.

It is still another object of the present invention to provide device which may be left in place on the patient during the early stages of emergency treatment through initial assessment of the degree of injury and proposed treatment. It is a further object of the invention that all of the components of the device be radio-lucent.

DISCLOSURE OF INVENTION

The present invention relates to a device and a method of rapidly immobilizing a fractured bone and particularly a fractured pelvic bone. The invention also provides a method and device which can be used in most instances to supply sufficient pressure at the site of the fracture to arrest bleeding that may accompany the fracture. The device of the invention may be easily and quickly applied to the patient with little regard to either the dimensions of the patient or the strength of the medical treatment personnel applying the device to the patient. The skill level required of the emergency personnel applying such a device to a patient suffering from a bone fracture is generally not significantly more than that required from such personnel at the present time in treating the same type of fracture. The device of the invention may be left in place both during the early stages of emergency treatment and through initial assessment of the degree of injury and proposed treatment. This includes conducting an x-ray examination and, accordingly, preferably, the device is free of radio-opaque materials. In addition, the device of the invention is so constructed and is formed from such materials as to permit the device to conform to the profile and the dimensions of the part of the body to which it is applied. Accordingly, except where a stay or splint type of article is to be operatively associated with the device, no rigid parts are incorporated into the device.

The orthotic trauma device is suitable for use in the emergent treatment of most types of bone fractures and preferably pelvic fractures. Compression of the pelvis with this orthotic device stabilizes the broken bones of the pelvis and helps control blood loss by reducing the volume that can be bled into. Reducing the motion of the bone fragments allows bleeding sites to clot off helping to limit blood loss as well as greatly improving the comfort of the patient. Use of this device lessens the likelihood of further injury to nerves, blood vessels or internal organs when the patient is moved. These devices can easily be applied at the accident scene by emergency medical technicians or in an emergency room. These devices provide sufficient provisional stabilization of the pelvis that the need for emergent application of a pelvic external fixator is eliminated in most cases.

This device does not interfere with the systematic evaluation of the trauma patient in the emergency room. It is preferably radiolucent and allows X-rays, CT scans, and angiography, abdominal ultrasound, peritoneal lavage, etc. to be carried out with the device in place. If need be it can be removed and reapplied easily. It can be left in place in most cases until workup is compete and definitive open reduction and internal fixation of the pelvic fracture can be performed.

The orthotic devices of the present invention, include an orthosis body or bracing portion, in the shape of a wide belt, adapted to be wrapped around a portion of a body of a user, the bracing portion being elongated and formed from a material which is easily cut with cloth-cutting scissors and is also, preferably, formed from a material which is radiolucent (i.e., non-radiopaque). A detachable fastening device is provided at the distal or outer ends of the elongated bracing portion to detachably secure the ends around the part of the body where the bone fracture is located. The fastening device is preferably provided with a means for adjusting the tightness or tension of the bracing portion, accomplished preferably by increasing the mechanical advantage of the fastening device. Preferably the means for increasing the mechanical advantage of the fastening device is a detachable pulley system which includes a pair of pulley banks. A first bank of the pulley system is detachably disposed on a first distal end of the elongated bracing portion and a second pulley bank is detachably disposed on a second distal end of the elongated bracing portion. A cable is operatively connected to the two pulley banks such that the first and second banks of the pulley system are in juxtaposed relationship. The cable runs through a pulley on each juxtaposed pulley bank in series and in alteration, shortening of the cable pulling the two banks of pulleys and concomitantly the opposed ends of the orthosis body together and tightening the orthotic device with the aid of mechanical advantage dependent upon the number of pulleys mounted in the pulley bank on each opposing orthosis body end.

In a preferred embodiment, each set of pulleys comprises two modular banks of pulleys which are detachably secured to opposing free ends of the same bracing portion. A cable is provided to connect pulleys in the opposing banks of pulleys in a set in series and in alteration. The ends of each cable preferably may be joined to form an endless cable or are attached to a handle which also achieves the effect of an endless cable. Preferably, the handle also may be removed from the body of the device when the modular banks of the pulley set are removed.

The orthotic device of the invention is easy to apply when used to immobilize most bone fractures. When used for immobilizing most pelvic fractures, the device can be placed on the exam table or gurney before the patient is placed thereon or it can be slid underneath the patient's hips. The belt may then be cut to the proper length with a scissors, such as the type commonly used in cutting adhesive tape and gauze. Preferably, when placed on the patient, there should be a gap of about of six inches at the front of the device between the belt or free ends of the orthosis body. The removable fastener is then detachably secured to each of the free ends of the orthosis body and suitably tightened to provide the appropriate amount of compression. In a preferred embodiment of the invention which employs a mechanism that increases the mechanical advantage of the fastening device, such as a pulley system which includes two banks of pulleys, each bank is then put in place on a respective belt end using a suitable fastener, such as a hook-and-loop means of attachment. The pulley system is then cinched tight and secured. Because of the combination of the orthosis body or belt of the invention and the characteristics of the fastening system employed, particularly the preferred pulley system of the invention, including both the structural features thereof and the materials used in the construction of the component parts, the orthotic trauma device achieves "isobaric compression", when tightened, meaning that the device applies substantially uniform pressure to all surfaces of the body with which it contacts. Since the belt or bracing portion itself is made of a soft material and the device provides isobaric compression, it can be left in place for a considerable length of time without causing pressure problems to the skin.

To improve appropriate immobilization when used to isolate a bone fracture located other than in the pelvic region, an embodiment of the present invention may include a rigid splint or stay, preferably held removably in place in the bracing portion. Preferably, the splint or stay would be disposed within a pocket in the bracing portion.

BRIEF DESCRIPTION OF DRAWINGS

Other objects, features and advantages will become evident in light of the following detailed description, considered in conjunction with the referenced drawings of preferred embodiments according to the present invention. It should be understood that these drawings are exemplary only and should not be construed as limiting the invention in any way.

MODES FOR CARRYING OUT THE INVENTION

Figure 1:
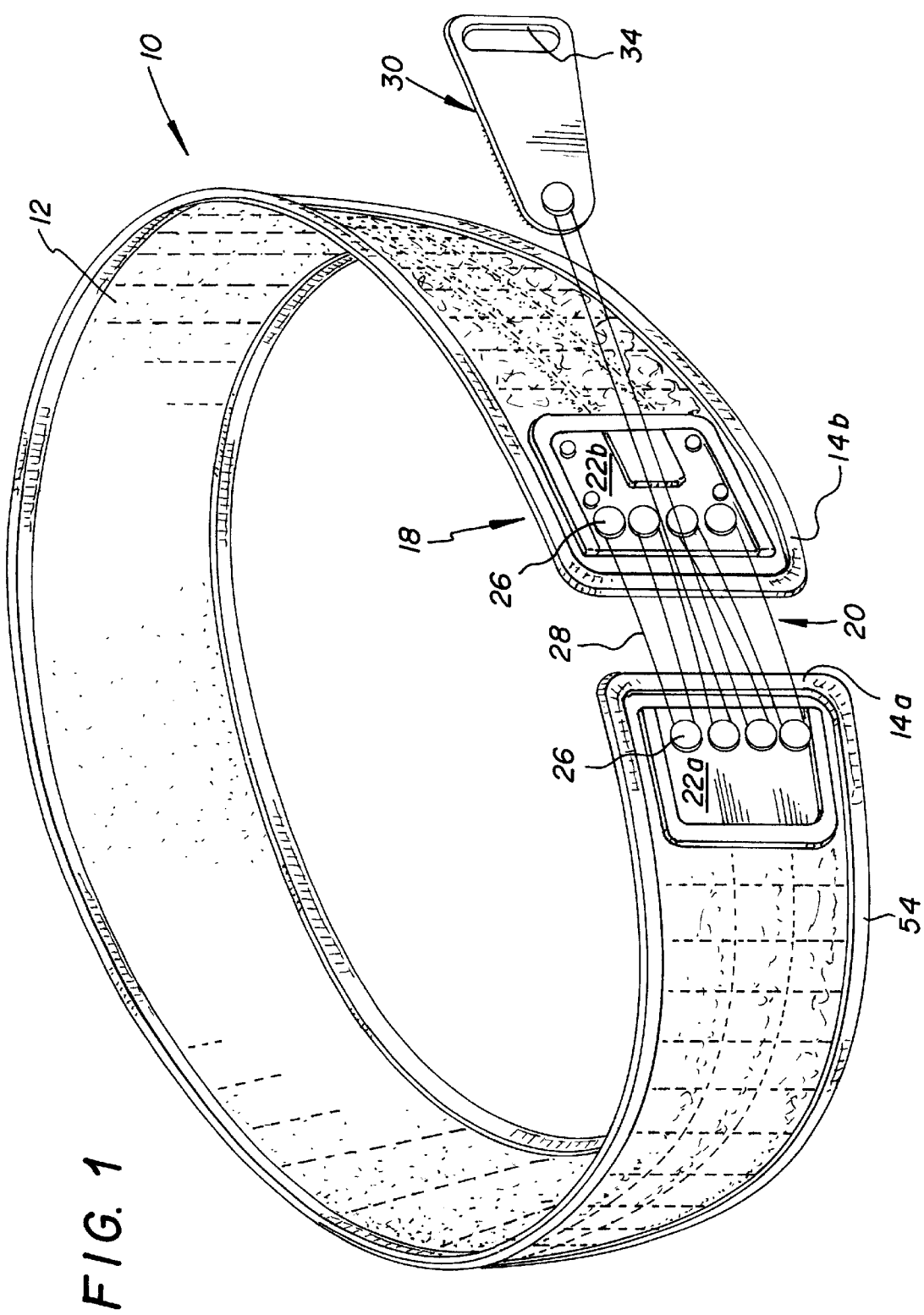
FIG. 1 shows a perspective view of a first embodiment of an orthotic device according to the present invention in an assembled position as it would be worn.

FIG. 1 shows a first embodiment of the present invention. FIG. 1 illustrates an orthotic trauma device 10 in an assembled position as it would be worn by a patient. The orthosis 10 includes a bracing portion or orthosis body 12, generally having a belt-like shape and made of a material suitable to achieve the type of support sought in treating the condition of the patient wearing the orthotic device. Typically this would include pliant and semi-rigid materials, although a more pliant material is generally preferred to conform substantially to the body of the wearer and to provide support but avoid causing pressure problems to the skin, such as the formation of blisters. The material from which the orthosis body is formed should also be easily cut by a scissors or shears, particularly of the type commonly used or found in hospitals, emergency medical facilities, ambulances, or first aid kits to cut various kinds of adhesive tape and gauze. Suitable materials include canvas, cotton, polyester, compressed polyester foam, blends of cotton and polyester, nylon, nylon mesh, etc. Preferred as the material from which the orthosis body is manufactured is a blend of cotton and polyester. Preferred as the material from which the orthosis body is formed is a blend of cotton and polyester. In other situations, where flexion is to be avoided, either a more rigid material is selected for all or a portion of the body of the orthosis or, more preferably, the orthotic device is used in conjunction with other component parts made from a more rigid material, such as rigid or semi-rigid stays or splints made from a rigid plastic or metal.

It may be noted that the term "rigid", as used herein to describe materials from which the orthoses of the invention are constructed, does not mean totally inflexible or unyielding, since many of materials employed can be bent when a sufficient force is applied to a surface of the material. These materials typically resume their original configurations when the deforming force is removed, however. As used in describing the materials from which the invention is constructed, rigidity refers to a resistance to deformation exhibited when in use.

In some instances, several layers may be employed in the orthosis body 12 to achieve different properties. For example, to achieve different strength characteristics or resistance to tearing, different materials may be employed in the same belt-shaped bracing portion in which an inner surface is intended to provide a soft contact surface and the outer surface is designed to removably engage a complementary portion of a hook-and-loop fastener surface and the bracing portion as a whole desirably provides fluid absorbency and containment properties. In a preferred embodiment of the invention, the bracing portion 12 includes three layers: an inner lining composed of nylon and polyester, preferably 80% woven nylon and 20% woven polyester, a core or intermediate layer of polyester, preferably 100% polyester foam, and an outer layer of polyethylene.

The elongated orthosis body 12 includes two free or distal ends, 14a and 14b. Although the bracing portion 12 may include a binding 54 at the peripheral edge thereof, it is preferred that not only the material from which the body portion 12 is formed but also the binding 54, when used, should be easily cut by a scissors. Stitching every 1" can be used as raveling preventors. This is important since it avoids the necessity of the emergency facility or ambulance of carrying a large inventory of different lengths or widths of the device. With only one or a few sizes of the device, generally any size body part of any size individual can be properly fit merely by cutting the device to a proper size. In most situations this can be accomplished by removing a portion of one of the free ends 14a or 14b.

The orthosis body 12 my also include vertical (i.e., substantially perpendicular to the longitudinal direction of the belt-like shape of the body 12) stitches (not shown) coextending substantially from upper edge 56a to lower edge 56b transverse to the longitudinal direction of the body 12. These stitches, provided substantially parallel to one another at intervals of from about ½ to about 3 inches, preferably about every inch, minimize the tendency of the material(s) to unravel or layers to separate (when more than a single layer is employed) once on of the free ends of the orthosis body is cut. As shown in another embodiment (FIG. 1), horizontal stitches may also be provided in the orthosis body.

On opposite distal or free ends 14a and 14b of each bracing portion or orthosis body 12 are provided complementary fastener or fastening means for securing the two free ends 14a and 14b together after the bracing portion 12 is wrapped around the afflicted body part of the patient. Although, buttons and button holes, snap fasteners, complimentary hook-and-loop fastener portions or other similar fasteners commonly used in garments may be employed to secure the free ends of the brace body 12 together by disposing the free ends in an overlapping manner, much preferred is a substantially fully adjustable type of fastener mounted on opposite free ends 14a and 14b of the bracing portion 12.

The preferred fastener or fastening means 18 includes a means for adjusting the tightness or tension of the orthotic trauma device on the patient. Preferably the tension adjusters used to custom fit the orthotic devices of the present invention to the profile of the body part of the individual wearer of these orthotic devices reduces the amount; of force required to apply suitable tension to the device by employing a mechanical advantage. The preferred means of individual adjustment using mechanical advantage is one which allows adjustment continuously over a wide range, rather than a stepwise or incremental adjustment obtained with some fastening systems. Most preferably, the individual adjuster using mechanical advantage includes a pulley set 20 which employs a pair of opposing banks of pulleys 22a and 22b. Each bank includes a plurality of individual pulleys 26 and a cable 28 is looped serially and in alteration around the pulleys 26 and is fixed at each end of the cable to a controlling device such as a handle, designated as 30, so as, in effect to form an endless cable. Although a cable which is anchored at one end and wound around each of the pulleys in a series could be used to achieve a suitable mechanical advantage and to accomplish the same degree of adjustment of the endless cable of the preferred embodiment of the invention, the cable would need to be pulled to twice the length of the preferred system in which the cable is anchored to a controlling or grasping device. This is not ergonomically desirable, nor even feasible, for the great majority of patients and applications.

Although element 26 is referred to herein as a "pulley", Illustrated in the figures and identified by reference numeral 26 are actually pulley housings. Each housing includes a circular collar provided with two slots for entrance and exit of the cable 28. Sealed to the top of each collar (preferably by sonic sealing means) is a mushroom-shaped cap. Within each housing is affixed a vertically disposed, centrally positioned spindle extending to almost the inner surface of the cap. Coaxially disposed and freely rotatable on the spindle is a pulley around which the cable travels.

Each component of the fastening system, including each component of the pulley system, is preferably formed from a material which is radiolucent. Preferred are plastic materials such as nylon or acetylene/butadiene/styrene (ABS) plastic, with the latter being most preferred for the reasons discussed below. The cable is formed from a strong, pliant material with woven polyester being preferred.

The number of pulleys provided in each bank of pulleys is determined by such factors as the amount of space provided for pulleys within each bank and the mechanical advantage being sought. The size of the particular bank of pulleys is determined in part by the size of the orthotic device and manufacturing considerations. Larger devices allow for concomitantly larger pulley sets and their respective banks of pulleys. The appropriate mechanical advantage is determined with a consideration of the strength of the medical personnel using the device and the volume of the portion of the body covered by the device. Generally, the pulley system used in the orthoses of the invention is constructed with an appropriate number of pulleys to provide a minimum of effort to achieve abdominal compression but not high enough to cause injury by over-tensioning the orthosis. Typically, this equates to a mechanical advantage for each pulley system in the range of about 2:1 to about 10:1, preferably about 4:1 to about 6:1, and most preferably about 4:1.

As illustrated in the figures, the ends of each cable 28 are preferably attached to a controlling or handle device for the set of pulleys 22. The device may include an easily graspable member, such as a cloth tab, loop, ring or bail. In the preferred embodiment, either a bail shaped member may be secured to the free end of the handle or, more preferably, a slot 34 may be formed proximate the free end of the handle 30. The handle 30 is formed, preferably, from plastic which is sufficiently flexible to assume, in use, substantially the same cross-sectional configuration or contour as the orthosis body 12 when the handle is removably secured to the outer surface of the orthosis body and the orthotic device is placed on a body part of the patient. Preferably, the handle 30 includes a means of detachably securing the handle 30 to a portion of the orthosis body 12 after adjustment has been made or the device has been removed from the wearer. Such means of securing could include a series of clasps or a buckle and strap arrangement. However, most preferred is a hook-and-loop arrangement. In such a system, a piece of hook-and-loop fabric is affixed to the underside of a portion of the handle member 30. Preferably, the hook-and-loop material used on the underside of the handle 30 is formed from nylon.

After adjustment has been made and the appropriate tension has been established in the cable 28, the handle may be releasably secured to a bracing portion 12 by placing the hook-and-loop fabric portion attached to the handle member 30 in contact with a portion of the complementary hook-and-loop material on the orthosis body 12. Either a portion of or, preferably, the entire outer surface of the orthosis body 12 is formed from a material which adheres to a complementary hook-and-loop material affixed to the underside of the handle 30.

Although the individual pulleys may be secured directly to the material from which the brace body 12 is formed, it is much preferred that they are secured to or formed as a modular unit with the pulleys secured to a plate, preferably the latter. It is also preferred that each pulley bank, 22a and 22b, be removably affixed to a corresponding free end 14a or 14b of the orthosis body 12. Although this may be accomplished using a variety of means, such as engaging eyelets and buttons or engaging snaps, considering that the orthosis body will frequently be cut to fit an injured body part, a hook-and-loop portion (not shown) permanently attached to the underside of the modular pulley bank is most preferred. This not only allows the freedom of placing the pulley banks 22a and 22b anywhere on the complementary hook-and-loop surface of the orthosis body but is additionally cost effective in manufacturing the device since it is unnecessary to provide snaps, buttonholes, buttons, etc. on the device, many of which would likely be removed during fitting of the device to the injured body part.

The orthotic trauma device of the present invention proves most effective in treating bone fractures in both emergency and non-emergency situations because of several features of the device. First, as indicated above, based on the materials used in the orthosis body and the mechanical advantage achieved with the pulley system of the fastening system, the device provides isobaric compression. However, the device of the invention also provides the ability to custom fit the device rapidly to any body part of any patient. This results not only from the ability to cut the orthosis body 12 quickly and easily with a pair of scissors, and the choice of pliant and supportive materials for the orthosis body, but also because of the choice of materials for the fastening system 18 and, preferably, the structure thereof.

The fastening system 18, preferably including the pulley banks 22a and 22b and the handle 30 are preferably formed from a semi-rigid plastic. Although the plastic, preferably used to form all of the parts of the pulley system 20 with the exception of the cable 28 and the hook-and-loop fabric fasteners, is flexible, it is not as flexible or pliant as the material from which the orthosis body is formed. Accordingly, while the term "semi-rigid" is used to describe the plastic from which each baseplate 25 of the pulley banks 22a/22b and handle 30 are formed, these components are formed from plastic parts having cross-sectional thicknesses which are thin enough to allow the components to flex and substantially conform to the surface contours of the body part which the respective portion of the orthotic device 10 contacts. ABS plastic is preferred as the material from which the pulleys 26, baseplates 25 and handle 30 are manufactured since it provides the appropriate flexibility and strength for the components.

Another preferred feature of the invention assists the orthotic trauma device in conforming to the surface contours of the body part on which the device is placed. In the preferred embodiment of the pulley system 20a, illustrated in FIGS. 2 and 3, pulleys 26 are mounted on baseplate projections or fingers 27. This manner of mounting the pulleys 26 allows the portion of the baseplate supporting each pulley (i.e., the projections 27) to flex above or below the "plane" of the baseplate independently of the other pulleys. As a result, when the orthotic device is in place on the body part, as the cable 28 is tightened, the baseplate projections 27 and their associated pulleys 26 individually and closely conform to the contours of the body part.

Figure 2:
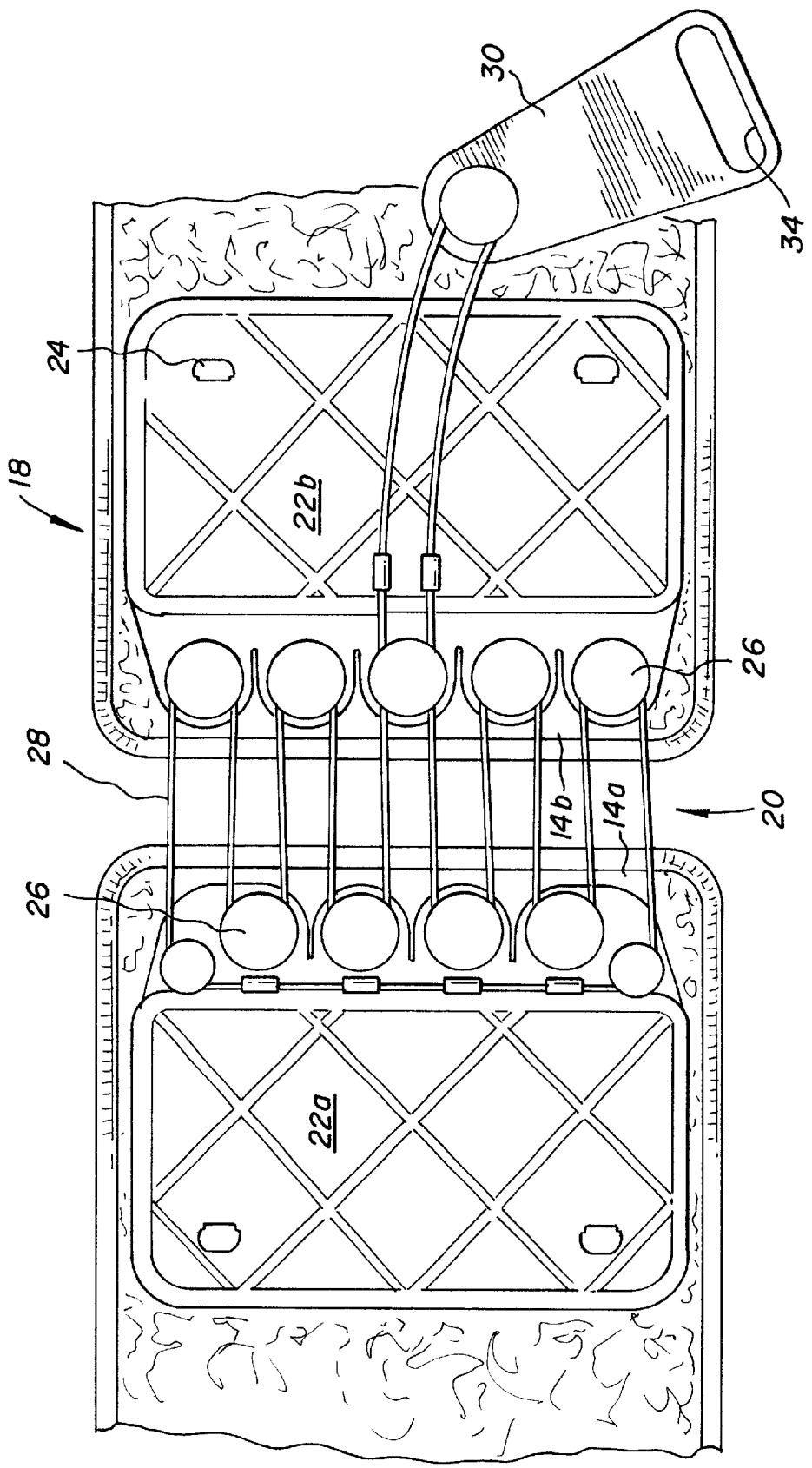
FIG. 2 illustrates a plan view of a preferred embodiment of a pulley set.
Figure 3:
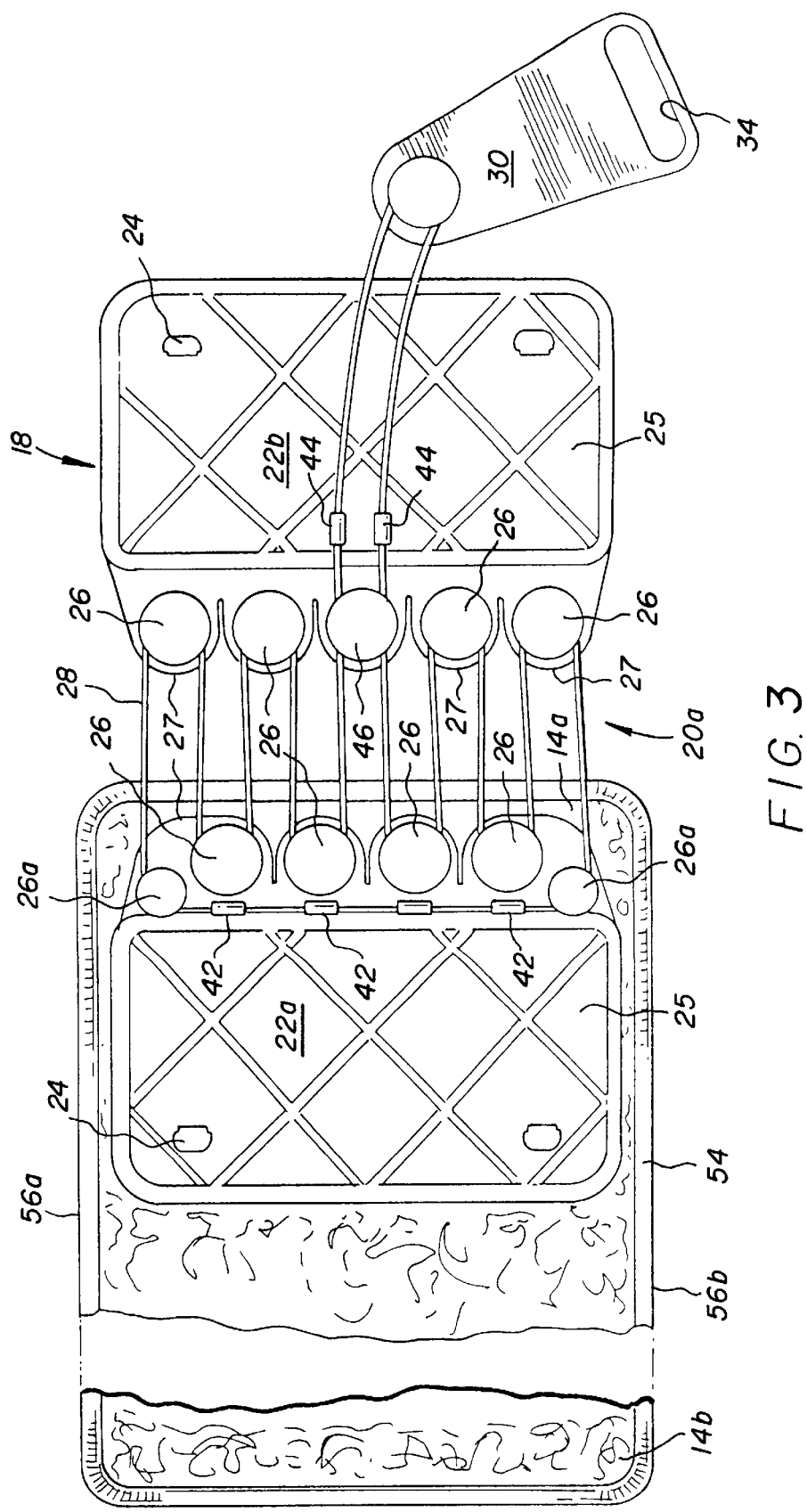
FIG. 3 is a plan view of a preferred embodiment of the present invention with the orthosis body in an extended position and one bank of a set of the modular pulley system removed from its corresponding free end of the orthotic device.

Another preferred embodiment of the pulley system of the invention allows the orthotic trauma device to both assume the contours of the body part on which the device is placed and to be rapidly and easily adjusted to custom fit the body part. This feature is shown in FIGS. 2 and 3, illustrating the preferred pulley system 20a. This feature includes a series of cable guides or channels 42, 44, and 46. The purpose of the cable guides is two fold: to minimize the chances of the cable 28 snagging on any object and to cause the cable to move in a direction which is as straight as possible except where the cable travels around a pulley. Accordingly, cable guides 42, shaped like tunnels, are arranged in series on pulley bank 22a in a line which is substantially parallel and spaced from a line imagined to pass through the centers of each of the pulleys 26 located on the same pulley bank 22a. A second set of cable guides 44 is provided on the juxtaposed pulley bank 22b. In contrast to the cable guides 42, cable guides 44 are disposed parallel to one another to guide the two ends of the cable 28 to the handle to which the cable ends are attached in a direction substantially perpendicular to a line imagined to pass through the centers of each of the pulleys 26 and cable guide 46 on the pulley bank 22b.

Cable guides 44 and 46 are preferably placed at approximately the center of the pulley bank 22b to facilitate placement of the pulley system 20a on the ends 14a and 14b of the orthosis body 12 without regard to the orientation of the position of the device on the patient or the position of the person fitting the device on the patient. Thus, were the position of the parallel disposed cable guides 44 (and 46) to be located at either the top or bottom of the pulley bank 22b, with certain orientations of the device and the medical personnel, when the handle is pulled, the angle formed between the segments of the cable 28 between the cable guides 44 and 46 and the cable guides 44 and the handle 30 would diverge sufficiently from 180 degrees to cause the cable to bind in the cable guides 44. Placement of the cable guides 44 and 46 close to the center of the pulley bank 22b minimizes such binding.

Although appearing to be a pulley housing in FIGS. 2 and 3, element 46 is really a cable guide having a configuration corresponding to that of a pulley housing. Cable guide 46 is provided with two sets of apertures (not shown): two "entrance" apertures spaced apart from one another on the side of the pulley bank 22b which faces pulley bank 22a where the cable from pulley bank 22a crosses over to pulley bank 22b and "enters" cable guide 46 and two "exit" apertures facing cable guides 44. Each of the entrance apertures and each of the exit apertures are spaced apart by a distance which is substantially the same as the distance separating the channels of the parallely arranged cable guides 44. This is done to maintain the ends of the cable 28 substantially parallel to one another.

Located at the upper and lower portions of the pulley bank 22a, proximate the first and last cable guides 42 in the series and proximate the first and last pulleys 26 on the pulley bank are cable guide pulleys 26a. While not functioning to alter the mechanical advantage of the fastening and tensioning system, since cable 28 trails around the pulley 26a for about 90 degrees, cable guide pulleys 26a serve the valuable function of ensuring that even though the spacing between the first and last pulleys 26 is different on the opposing pulley banks 22a and 22b (there are four pulleys 26 on pulley bank 22a but four pulleys 26 and cable guide 46 arranged in a single row on pulley bank 22b), each segment of the cable 28 passing between opposing pulleys 26 (and cable guide 46) is substantially parallel to an adjacent segment of cable 28. As a result, this arrangement, including the cable guide pulleys 26a, permits the rapid adjustment and tightening of the orthotic device even when the contours of the body part on which the device is placed cause the facing edges of the pulley banks 22a and 22b to assume a non-parallel orientation.

In using the invention, the orthosis body 12 is cut to fit the injured part of the patient's body. Thereafter, the orthosis body is placed around the part of the body having the fracture and the pulley banks 22a and 22b are removably secured to the free ends 14a and 14b, respectively, of the orthosis body 12. The orthotic trauma device 10 is positioned such that the pulley set 20 is accessible. Typically, this results in the pulley set being positioned at the front of the body. The handle 30 is then pulled to adjust the tension of the pulley set to achieve the appropriate compression sought. If the length of the cable 28 between the pulleys 26 and the handle 30 is excessive, the slack may be taken up by winding a portion of the cable around one of the pegs 24 disposed at the corners of the pulley banks 22a or 22b. After adjustment, the side of the handle with the hook-and-loop material thereon is merely pressed against the complementary hook-and-loop material on the outer surface of the orthosis body 12.

The orthotic device of the invention is intended to be used primarily in treating bone fractures as a result of trauma. However, because of the ease of use, effectiveness in applying uniform compression to an injured body part, and speed of assembly and placement on a patient, the device could be used with other component parts to form other orthotic devices. For example, the pulley system of the present invention and a bracing portion or body brace may be combined with a rigid front piece, a sternal notch piece, movably and adjustably secured to the rigid front piece, and a rigid rear piece, removably and adjustably secured to the rigid front piece to form a thoracic lumbar sacral orthosis. Alternatively, the pulley system of the present invention and a bracing portion or body brace may be used to form a lumbar sacral orthosis.

What is claimed is:

1. An orthotic device comprising:
   a unitary elongated orthosis body having first and second distal ends, the orthosis body being in a form of a belt having a uniform width, and adapted to be wrapped circumferentially around a portion of a body of a wearer of the device, the orthosis body being formed of a pliant material which is adapted to be easily cut with cloth-cutting scissors;
   a detachable fastening device releasably connected to the first and second distal ends, respectively, of the elongated orthosis body; and
   means for adjusting the tightness of the orthosis body operatively associated with the detachable fastening device whereby uniform compression is provided circumferentially around the entire portion of the body of the wearer and in a width direction along substantially the entire width of the belt;
   whereby the uniform compression immobilizes the portion of the body wrapped therein.

2. An orthopedic trauma device according to claim 1, wherein said means for adjusting the tightness of the orthosis body comprises a means for increasing the mechanical advantage of the fastening device.

3. An orthopedic trauma device according to claim 2, wherein said mechanical advantage increasing means comprises a pulley system, said pulley system including:
   a pair of pulley banks arranged in juxtaposed relationship, a first bank of which is detachably disposed on a first distal end of the elongated orthosis body and a second bank of pulleys detachably disposed on a second distal end of the elongated orthosis body; and
   a cable interconnecting the two pulley banks and running through a pulley on each of the pulley banks in alteration, shortening of the cable pulling the pulley banks together and tightening the orthotic device with the aid of a mechanical advantage dependent upon the number of pulleys mounted on each of the pulley banks.

4. An orthotic device according to claim 3, wherein the pulley system provided with cable guides to arrange all sections of cable between opposing pulleys parallel to one another.

5. An orthotic device according to claim 3, wherein each set of pulleys with an associated cable provides a mechanical advantage of about 2:1 to about 10:1.

6. An orthotic device according to claim 3, wherein said cable has two free ends secured to a handle element.

7. An orthotic device according to claim 6, wherein said handle element is formed from a flexible material.

8. An orthotic device according to claim 3, wherein each bank of pulleys includes a plate on which pulleys are mounted, said plate being detachably secured on a distal end of said elongated orthosis body.

9. An orthotic device according to claim 8, wherein said plate is detachably secured by means of portions of hook-and-loop fastener material disposed on at least a portion of said plate which engages complimentary portions of hook-and-loop material on a surface of the elongated orthotic body.

10. An orthotic device according to claim 1, wherein the orthosis body is formed of radio-lucent material.

11. An orthotic device according to claim 1, wherein the fastening device is formed from a radio-lucent material.

12. An orthotic trauma device, comprising:

an elongated orthosis body having a continuous length with opposing distal free end portions, the entire continuous length being fabricated from one of hook material and loop material;

a mechanical advantage device including a first baseplate releasably connected to one of said opposing distal free end portions of the orthosis body, a second baseplate releasably connected to the remaining opposing distal free end portion of the orthosis body and a cable interconnecting the first and second baseplates, the cable having a first cable portion extending between the first and second baseplates in alternation and a second cable portion connected to the first cable portion; and a handle connected to the second cable portion and fabricated from a remaining one of the hook material and the loop material.

13. An orthotic trauma device according to claim 12, wherein each one of the first and second baseplates includes a plurality of pivot elements wherein the first cable portion pivots about sequential ones of the pivot elements.

14. An orthotic trauma device according to claim 13, wherein each one of the pivot elements is a pulley.

15. An orthotic trauma device according to claim 12, wherein the mechanical advantage device includes a pulley system having a pair of pulley banks with each pulley bank formed with a respective one of the first and second baseplates such that the first cable portion runs through a respective pulley on each of the pulley banks in alteration.

16. An orthotic trauma device according to claim 15, wherein upon pulling the handle when the first and second baseplates are releasably connected to the respective distal free end portions, the distal free end portions move toward each other.

17. An orthotic trauma device according to claim 12, wherein the elongated orthosis device forms a belt having a uniform width.

18. An orthotic trauma device according to claim 17, wherein each one of the first and second baseplates extends substantially along the uniform width of the belt.

* * * * *